(12) United States Patent
Tixier et al.

(10) Patent No.: US 9,182,360 B2
(45) Date of Patent: Nov. 10, 2015

(54) MULTI-FREQUENCY MICROWAVE SENSOR FOR TEMPERATURE INDEPENDENT MEASUREMENT OF MOISTURE

(71) Applicants: Sebastien Tixier, North Vancouver (CA); Michael Kon Yew Hughes, Vancouver (CA)

(72) Inventors: Sebastien Tixier, North Vancouver (CA); Michael Kon Yew Hughes, Vancouver (CA)

(73) Assignee: Honeywell ASCA Inc., Mississauga (CA)

(*) Notice: Subject to any disclaimer, the term of this patent is extended or adjusted under 35 U.S.C. 154(b) by 310 days.

(21) Appl. No.: 13/947,644

(22) Filed: Jul. 22, 2013

(65) Prior Publication Data

US 2015/0022220 A1 Jan. 22, 2015

(51) Int. Cl.
| | |
|---|---|
| *G01N 22/00* | (2006.01) |
| *G01N 22/04* | (2006.01) |
| *D21F 7/00* | (2006.01) |
| *D21G 9/00* | (2006.01) |
| *G01N 33/34* | (2006.01) |

(52) U.S. Cl.
CPC ............... *G01N 22/04* (2013.01); *D21F 7/003* (2013.01); *D21G 9/0036* (2013.01); *G01N 33/346* (2013.01)

(58) Field of Classification Search
CPC .............................. G01N 22/04; G01N 33/346
USPC ........................................................ 324/640
See application file for complete search history.

(56) References Cited

U.S. PATENT DOCUMENTS

| | | | |
|---|---|---|---|
| 5,233,306 A | 8/1993 | Misra | |
| 5,315,258 A * | 5/1994 | Jakkula et al. | 324/640 |
| 5,455,177 A | 10/1995 | Krause | |
| 5,744,971 A | 4/1998 | Chan | |
| 5,965,888 A | 10/1999 | Engstrom | |
| 6,223,133 B1 | 4/2001 | Brown | |
| 6,507,401 B1 | 1/2003 | Turner | |
| 6,525,319 B2 | 2/2003 | Meglen | |
| 6,606,568 B2 | 8/2003 | Meglen | |
| 6,617,861 B1 | 9/2003 | Joshi | |
| 6,856,140 B2 | 2/2005 | Talanov | |
| 7,061,251 B2 * | 6/2006 | Taylor et al. | 324/534 |
| 7,494,567 B2 | 2/2009 | Haran | |
| 7,756,558 B2 | 7/2010 | Ridder | |

(Continued)

OTHER PUBLICATIONS

European Patent Office Search Report for EP 14 17 6222 Nov, 3, 2014.

(Continued)

*Primary Examiner* — Jeff Natalini
(74) *Attorney, Agent, or Firm* — Cascio Schmoyer & Zervas

(57) ABSTRACT

Microwave techniques for measuring moisture and other properties of paper and related products without requiring an independent measurement of temperature are provided. A sensor directly measures the reflection or transmission of microwaves at a number of well-chosen frequencies so as to characterize the absorption spectrum of the product. The technique of measuring the parameters of a composition includes: (a) directing incident microwave radiation over a spectrum of wavelengths from an antenna upon the composition; (b) measuring the microwave radiation over the spectrum of wavelengths that emerges from the composition; (c) determining the reflected and/or transmitted transfer function; and (d) relating the transfer function of the composition to the parameters of the composition by applying a theoretic, calibrated, or hybrid model. The product moisture and temperature are extracted from the transfer function.

20 Claims, 3 Drawing Sheets

(56) References Cited

U.S. PATENT DOCUMENTS

| | | | |
|---|---|---|---|
| 7,911,345 B2 | 3/2011 | Potyrailo | |
| 7,956,327 B2 | 6/2011 | Shelley | |
| 8,354,849 B2 | 1/2013 | Richter | |
| 2002/0057095 A1* | 5/2002 | Zoughi et al. | 324/646 |
| 2006/0208194 A1 | 9/2006 | Typpo | |
| 2010/0295556 A1* | 11/2010 | Richter | 324/640 |

OTHER PUBLICATIONS

Archibald et al: "Regression Analysis of Microwave Spectra for Temperature-Independent Determination of Wheat Moisture Content", Applied Spectroscopy, Nov. 1, 1998 pp. 1435-1446.

Arie D. Dane et al: "The determination of moisture in tobacco by guided microwave spectroscopy and multivariate calibration", Analytica Chemica Acta, vol. 429, No. 2 Feb. 1, 2001.

Knochel, Reinhard, et al. "Stray Field Ring Resonators and a Novel Trough Guide Resonator for Precise Microwave Moisture and Density Measurements"; Measurement Science and Technology 18 (2007) pp. 1061-1068.

Pirk, Norbert "Methane Emission Peaks from Permafrost Environments: Using Ultra Wideband Spectroscopy, Sub-Surface Pressure Sensing and Finite Element Solving as Means of Their Exploration" Department of Physics, 2009, Lund University, Solvegatan 14, S-223 62 Lund, Sweden Seminar Series nr 174.

Sachs, J., et al. "Liquid and Moisture Sensing by Ultra-Wideband Pseudo-noise Sequence Signals" Measurement Science and Technology 18 (2007) pp. 1074-1087.

Volgyi, Ferenc "Design of an On-line Sensor with Spread-Spectrum and Modulated Backscatter Techniques" Subsurface and Surface Sensing Technologies and Applications III, Cam Nguyen Proceedings of SPIE vol. 4491, 151 (Nov. 27, 2001).

* cited by examiner

MULTI-FREQUENCY MICROWAVE SENSOR FOR TEMPERATURE INDEPENDENT MEASUREMENT OF MOISTURE

FIELD OF THE INVENTION

The present invention generally relates to microwave sensor techniques for measuring water in a composition and particularly to a microwave sensor for temperature independent measurements of moisture and other properties in paper, board, cellulose-based feedstock and the like.

BACKGROUND OF THE INVENTION

Various sensor systems have been developed for detecting sheet properties "on-line," such as in a papermaking machine while it is operating. Online control of the moisture content in feedstock such as wood chips and products such as oriented strand board (OSB) and paper board is highly desirable to improve production yield and product quality. Moisture in wood chips is one of the main parameters affecting the production of OSB and biofuels. For example, moisture critically affects the pyrolysis of wood products for the production of biofuels. Online moisture measurements are typically performed using either infrared or microwave absorption or spectroscopy techniques. Infrared techniques are limited to measuring surface moisture and/or low basis weight products due to the low penetration depth of infrared light. They cannot be successfully applied to thick products like wood chips in which moisture stratification is often present. Infrared techniques are also strongly affected by broadband absorbers such as elemental carbon that can be found in various products, in particular recycled paper products.

The most commonly used microwave method of measuring the water content on-line on a paper machine is the resonant-cavity technique. In this technique, the paper travels between the two half cavities of the sensor. The method consists of measuring the change in frequencies of two resonances due to changes in the water content in paper. The two frequencies used include one where the maximum amplitude of the electric field is in the middle of the cavity (i.e. at the paper location) and one where the minimum of the electric field (node) is in the middle of the cavity. The former is called the measure frequency and is most sensitive to the change in dielectric constant in paper (i.e. water content). The measure frequency is approximately 1.8 GHz. The latter is called the reference frequency and is mostly insensitive to changes in the dielectric properties in paper. The reference frequency is approximately 3 GHz. The reference frequency is used to correct for undesirable effects that affect both frequencies such as a slight change in the distance between the two half cavities. This resonant cavity method is quite sensitive to changes in water content but requires a separate temperature measurement in order to be accurate since the resonant-microwave technique is strongly affected by the temperature of the sample being measured. The reason is that the permittivity of water in the microwave range is very temperature sensitive. Thus, microwave sensors generally require an independent temperature measurement being performed as well as a temperature correction algorithm. The temperature corrector applied can be as large as 0.5% moisture per 10° C. change in the sheet temperature. Furthermore, this method provides only a water weight measurement. An independent sensor such as a beta- or gamma-emitter-based sensor is required to measure basis weight. A percent moisture measurement is extracted from the water weight and basis weight measurements.

SUMMARY OF THE INVENTION

The present invention is directed to microwave techniques for measuring a cellulose-based product's average moisture and other properties accurately without requiring an independent measurement of temperature. The inventive microwave sensor can provide a measurement of the product temperature but since the microwave sensor does not use a resonant cavity it is not limited to the measurement frequencies sustained by the cavity. The microwave sensor directly measures the reflection or transmission of microwaves at a number of frequencies so as to characterize the reflection or transmission transfer function of the product under test. The product moisture and temperature are extracted from the aforementioned transfer function.

The microwave region of interest for moisture measurements is the 1 MHz-1000 GHz (1 THz) range. In this range the dielectric properties of water change dramatically. Measurements must be made in this range such that the measured reflection or transmission function of the sample is sensitive to water content as well as to the sample's temperature. In the case where only free water is present in the sample, a restricted microwave range of 1 GHz to 100 GHz is adequate. Bound water behaves differently to free water. Measurements at higher frequencies are required to detect bound water.

Water is a substance which strongly interacts with microwaves. The spectrum of absorption by water is highly specific and is well known. Furthermore the microwave spectrum is highly dependent on the product's temperature. The effect of temperature on the water absorption spectrum can be easily calculated using known equations. The microwave sensor of the present invention measures the reflection or transmission transfer function of a sample at a number of microwave frequencies. This transfer function characterizes the change in amplitude of the microwave radiation reflecting off or transmitting through a sample. The sample transfer function is measured at various frequencies in the frequency range where the permittivity of water changes dramatically. At low frequencies, the dielectric constant (real part of the permittivity) is high and is fairly independent of the frequency. Similarly, the dielectric loss (complex part of the permittivity) is low. At intermediate frequencies, around the inverse of the relaxation time of the water molecules, the dielectric constant drops dramatically with frequency. The dielectric loss peaks in this frequency range. Therefore, both the dielectric constant and the dielectric loss are very sensitive to the water temperature in this frequency range. This is explained by the fact that the relaxation time of the water molecules is a function of temperature. In the higher frequency range, the dielectric constant and dielectric loss are both low. Microwave radiation does not interact as much with water in this frequency range as it does at lower frequencies. The high frequency range is correspondingly a range where the relative influence of the dry product composition or dry product weight on the microwave reflection and transmission is the greatest.

By measuring the reflection and/or transmission of microwaves at frequencies in the low, medium and high ranges, the product transfer function is characterized in the regions where water, product temperature and dry product composition and weight play a role. Both moisture, in percent or water weight as well as temperature, can be accurately extracted from the measured transfer functions by applying a calibration. Calibrations are produced by relating measured transfer functions of samples with known compositions, measured at various temperatures.

The sample transfer function (Tf) is determined by taking the ratio of the measured amplitudes with the sensor interacting with the sample ($A_{amp}$) and with the sensor exposed to free space ($A_{free}$):

$$Tf = \frac{A_{smp}}{A_{free}}.$$

In one aspect, the invention is directed to a method of measuring one or more parameters of a composition that includes the steps of:

directing microwave radiation over a spectrum of wavelengths from an antenna to be incident upon the composition;

measuring the microwave radiation over the spectrum of wavelengths that emerges from the composition;

determining the reflected and/or transmitted transfer function of the composition over the spectrum of wavelengths; and relating the determined transfer function of the composition over the spectrum of wavelengths to one or more parameters of the composition by applying a model, with the proviso that an independent temperature measurement of the composition is not required.

In another aspect, the invention is directed to a sensor for measuring at least one property of a composition of a sample that includes:

a light source, which emits microwave radiation over as spectrum of wavelengths at a sample of the composition;

a receiver operable to detect reflected or transmitted radiation from the sample and to provide electrical detection signals;

signal generator that generates first signals to the light source to cause the light source to emit microwave radiation at two or more frequencies at the sample and second signals that are indicative of the two or more frequencies; and a processor that receives the electrical detection signals and the second signal and that is operable to determine at least one property of the composition by applying a model, with the proviso that an independent temperature measurement of the composition is not required.

The model can be derived solely from calibrations or it can be based on theoretical assumptions or is derived from a combination of both. A calibration model uses a set of known samples to predict the moisture content or other properties of paper board, OSB, cellulose-based feedstock and the like especially products that are thick. For example, representative paper samples with known water content in the range of interest, which is typically 0% to 10% water for the dry-end and 45% to 65% for the wet-end of the paper machine, are analyzed with the microwave sensor to generate amplitude measurements. The data derived from amplitude measurements together with the moisture content and the sheet temperature are used in a calibration model, which uses multivariate analysis to predict the moisture properties of paper during production. The multivariate analysis can be performed to standard techniques, including, Projection to Latent Structures (PLS), Principal Component Analysis (PCA), Partial Least Squares Regression (PLSR), Principal Component Regression (PCR), Multilinear Regression Analysis (MLR) or Discriminate Analysis.

DESCRIPTION OF PREFERRED EMBODIMENTS

Figure 1:
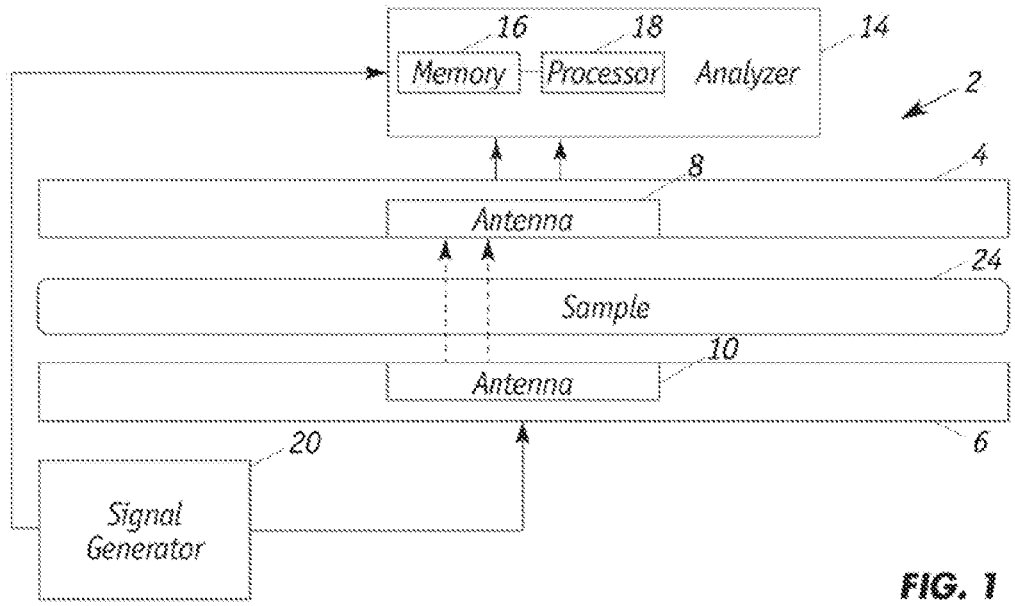
FIG. 1 shows an embodiment of the microwave sensor operating in the transmission mode.

FIG. 1 illustrates microwave sensor 2 in which signals of the frequency range of interest are synthesized by to signal generator 20 and the signals are amplified by power amplifier 22 and sent to antenna 10 where the electrical signals are converted to microwave signals in the required frequency range. Incident microwaves interact with the composition of sample 24 and emerging microwave radiation, having been attenuated and delayed in the process, is detected by antenna 8 which generates representative electrical signals that can be optionally amplified before being received by analyzer 14 which includes memory 16 and processor 18. In particular, the representative electrical signals correspond to the intensity of the transmitted radiation from sample 24. Analyzer 14 calculates the moisture and temperature and other parameters of interest from signals that are generated by antenna 10 and received by antenna 8. In this embodiment, antennas 8 and 10 are incorporated within scanner heads 4 and 6, respectively, so that the microwave device can be positioned onto a scanner to continuously measure across a moving web of the material.

In a preferred embodiment, microwave sensor 2 employs a signal generator 20 that generates microwave signals in the desired wavelength region by conventional apparatuses such as with that found in a Vector Network Analyzer (VNA). The frequencies can be stepped through the region in discrete steps or be swept through the range of interest.

Antenna 10 is capable of generating a signal across the frequency range of interest (5-1000 GHz for example). When a wide bandwidth is employed, it may be necessary to direct different parts of the spectrum to different antennae. Suitable antennas include horn antennae with ranges from 2-18 GHz and 18-40 GHz and other antennae designs for higher frequencies.

Signal generator 20 also provides synchronizing signals so the steps of directing radiation to sample 24 and measuring reflected or transmitted radiation from sample 24 are synchronized.

Signal processor 18 is coupled to antenna 8 to receive the electrical detection signals. Memory 16 stores calibration and normalization data to permit calculation of the moisture content, basis weight and other properties in the case where material 50 is paper. Processor 18 combines the signals received to determine at least one property of the material.

As shown in FIG. 1, when operating in the transmissive mode, the microwave source can be housed in sensor head 6 and microwave receiver 8 can be housed in sensor head 4 that is on the opposite side of material 24. The microwave sensor can also operate in the reflective mode, in which case, both microwave source and receiver are positioned on the same side as material 24. In this case, only a single antenna may be used and the transmitted and received signal electronically separated with a device such as a directional coupler.

Calibration Technique

Once the reflected and/or transmitted transfer function has been obtained, using techniques described above, the properties of interest such as moisture and sheet temperature can be obtained using a calibration.

The calibration can be performed in two different ways. The most direct calibration technique can be referred to as a one step calibration. The second method requires two main steps. Both techniques are described below.

The one step calibration technique is the most direct calibration method. No attempt is made to fit the transfer function. The measured transfer function is used in a multivariate analysis such as Principal Component Analysis (PCA) or a multiple regression analysis to predict the properties of interest (moisture, sheet temperature, etc.).

The calibration equation can take various forms. However, in the simplest case, a polynomial relationship of second order between the properties of interest (moisture and sheet temperature) and the measured transfer function is obtained such as in Eq. 1:

$$\begin{pmatrix} \text{Moist} \\ \text{STemp} \end{pmatrix} = \begin{pmatrix} a_{11} & a_{21} & a_{31} & a_{31} & \cdots \\ b_{11} & b_{21} & b_{31} & b_{41} & \cdots \end{pmatrix} \begin{pmatrix} Tf_1 \\ Tf_2 \\ Tf_3 \\ Tf_4 \\ \cdots \end{pmatrix} + \begin{pmatrix} a_{12} & a_{22} & a_{32} & a_{42} & \cdots \\ b_{12} & b_{22} & b_{32} & b_{42} & \cdots \end{pmatrix} \begin{pmatrix} Tf_1 \\ Tf_2 \\ Tf_3 \\ Tf_4 \\ \cdots \end{pmatrix}^2 \quad (1)$$

Where $Tf_n$ are the amplitude transfer values at various frequencies and $a_n$, $b_n$ are the calibration parameters.

The second calibration technique requires two main steps. The first step is a fit of the transfer function using a simplified model of the material. From the fit, a finite number of parameters are obtained. The second step is a multivariate analysis such as Principal Component Analysis (PCA) or as multiple regression analysis to relate the fit parameters to the physical properties of the material under test (moisture, sheet temperature, etc.).

Step 1

The fit is performed by considering an approximate model of the transfer function. In the case of a transmission transfer function, Tf can be approximated by:

$$Tf = T_1 \cdot T_2 \cdot e^{ik_0 n^* L}$$

Where $T_1$ and $T_2$ are the Fresnel amplitude transmission through the sample, $n^*$ is the complex index of refraction of the sample, L is the sample thickness and $k_0$ is the wavenumber in vacuum.

$$k_0 = \frac{2\pi f}{c},$$

where f is the frequency of the microwave radiation and c is the speed of light in vacuum.

The transmissions $T_1$ and $T_2$ characterize the transmission of light from free space to the sample and from the sample to free space. In the case of light transmission along the surface normal, they equate to:

$$T_1 = \frac{2}{1+n^*} \text{ and } T_2 = \frac{2 \cdot n^*}{1+n^*}$$

A similar model for the transfer function can be obtained for the case of a reflection sensor geometry.

The complex index of refraction $n^* = n + ik$ can be separated into two parts: a real part (n) and an imaginary part (k). The index of refraction is related to the complex permittivity as follows:

$$n^* = n + ik = \sqrt{\in} = \sqrt{\in' + i\in''}$$

where $\in$ is the complex permittivity of the sample.

The transfer function model can include a model of the complex permittivity. In the case of free water, the simplest model that can be used is the Debye relaxation model which is further described in Deybe P, *Polar Molecules*, New York: Chemical Catalog, 1929.

$$\varepsilon = \varepsilon_\infty + \frac{\varepsilon_0 - \varepsilon_\infty}{1 + i\frac{f}{f_0}} \quad (2)$$

Where $\in$ is the material permittivity, $\in_0$ is the static permittivity of water, $\in_\infty$ is the water permittivity at high frequency, f is the measurement frequency and $f_0$ is the relaxation frequency of water. Both $\in_0$ and $f_0$ are very temperature dependent In the case of free water in a low dielectric medium like paper, Eq. 2 can still apply but a constant term characterizing the dielectric constant of the medium must be added. In low moisture application (<10%), a sizeable amount of water in paper is not free but bound to the cellulose fibers. If the bound water is modeled name a similar Debye relaxation model as free water, a more precise model for the permittivity of paper is as follows:

$$\varepsilon = \varepsilon_{\infty m} + \frac{\varepsilon_0 - \varepsilon_\infty}{1 + i\frac{f}{f_0}} + \frac{\varepsilon_{0bw} - \varepsilon_{\infty bw}}{1 + i\frac{f}{f_{0bw}}} \quad (3)$$

Where $\in_{\infty m}$ is the high frequency permittivity of the mixture (i.e. material), $\in_{0bw}$ is the static permittivity of bound water, $\in_{\infty bw}$ is the bound water permittivity at high frequency, and $f_{0bw}$ is the relaxation frequency of bound water. $\in_{0bw}$ is typically smaller than $\in_0$. (See, F. Ulaby, R. Moore, and A. Fung, *Microwave remote sensing: Active and Passive*, Vol. III, *From Theory to Applications*, Norwood, Mass.: Artect House, 1986.) The high frequency permittivity of the mixture ($\in_{\infty m}$) is not expected to change significantly with temperature.

In the case where the relaxation frequency is not well defined or sharp and can be fitted with an associated width, the Davidson-Cole function can be used to model the permit tivity curve. (See, Cole R H and Davidson D W, J. Chem. Phys. 20, 1389-1391, 1952.):

$$\varepsilon = \varepsilon_\infty + \frac{\varepsilon_0 - \varepsilon_\infty}{\left(1 + i\frac{f}{f_0}\right)^{(1-\alpha)}} \quad (4)$$

Where $\alpha$ ($0<\alpha<1$) characterizes the width of the relaxation frequency distribution. Finally, for processes where additives present modify the conductivity of the material or if measuring in aqueous solution, the conductivity may need to be modeled:

$$\varepsilon = i\frac{\sigma}{2\pi\varepsilon_0 f} \quad (5)$$

Where $\sigma$ is the material conductivity and $\in_0$ is now the permittivity of free space. In order to fit the transfer function any combination of Eq. 2 to Eq. 5 may be required. The main criterion for selecting the fit function is the goodness of the prediction of the material properties.

If all fails, any fitting equations including polynomial, exponential, power laws, etc and a combination of all can be used to fit the transfer function.

Step 2

Once fit parameters to the transfer function have been obtained ($P_1, P_2, P_3, \ldots$), the material properties need to be calculated using a calibration equation. The calibration equation can take various forms and is typically based on Principal Component Analysis. However, in the simplest case, a linear relationship between the properties of interest (moisture and sheet temperature) and the fit parameters is obtained:

$$\begin{pmatrix} \text{Moist} \\ \text{STemp} \end{pmatrix} = \begin{pmatrix} a_1 & a_2 & a_3 & a_4 & \ldots \\ b_1 & b_2 & b_3 & b_4 & \ldots \end{pmatrix} \begin{pmatrix} P_1 \\ P_2 \\ P_3 \\ P_4 \\ \ldots \end{pmatrix} \quad (6)$$

Where $P_n$ are the fit parameters from the transfer function and $a_n$, $b_n$ are the calibration parameters.

With both calibration techniques, the calibration parameters are obtained by doing multiple regression analysis or PCA on data measured by the sensor using a set of calibration samples. The calibration samples are chosen so that the properties of these samples vary at least as much as what is observed during the manufacturing process. For example, in the case of a moisture measurement in paper or board, calibration samples that contain the range of basis weight, moisture, composition (or grade) and sheet temperature observed on the process must be prepared. In order to obtain a range of moisture, the samples may need to be bagged in ACLAR® brand bags or encapsulated in glass. Wet samples can be measured with the sensor as the moisture drops due to natural evaporation. Similarly, hot glass encapsulated samples can be measured continuously as the sheet temperature decreases naturally.

The material properties are measured online by first collecting the transfer function of the samples over an adequate frequency range in the 1 MHz-1000 GHz range. Second, the material properties such as moisture and sheet temperature are calculated using one of the calibrations obtained as per above (Eq. 1 or Eq. 6). In the preferred embodiment, the moisture content (in percent) of the paper product as well as its temperature are measured. The percent moisture measurement does not require the use of a nuclear radiation sensor.

Figure 2:
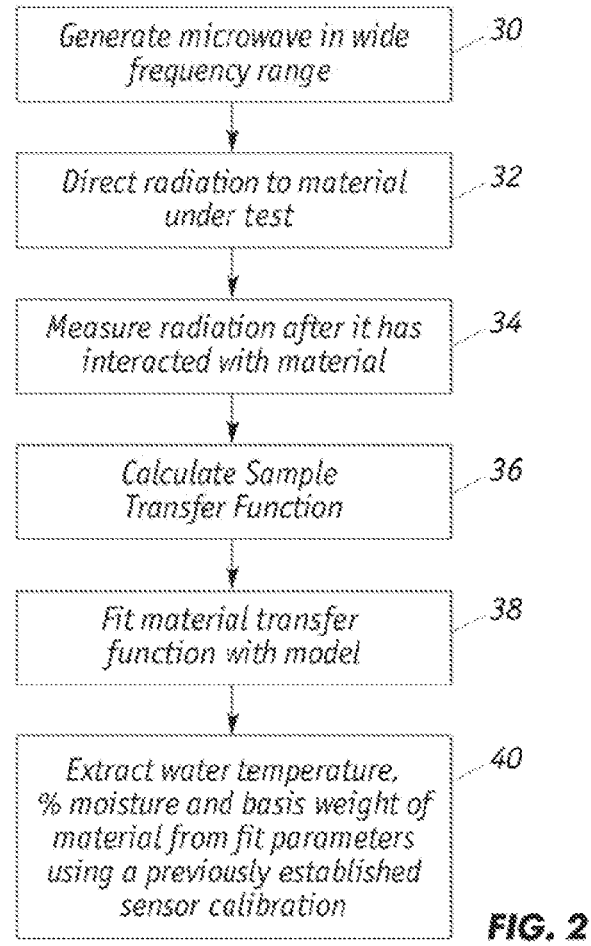
FIG. 2 depicts a measurement process for moisture calculations.
Figure 3:
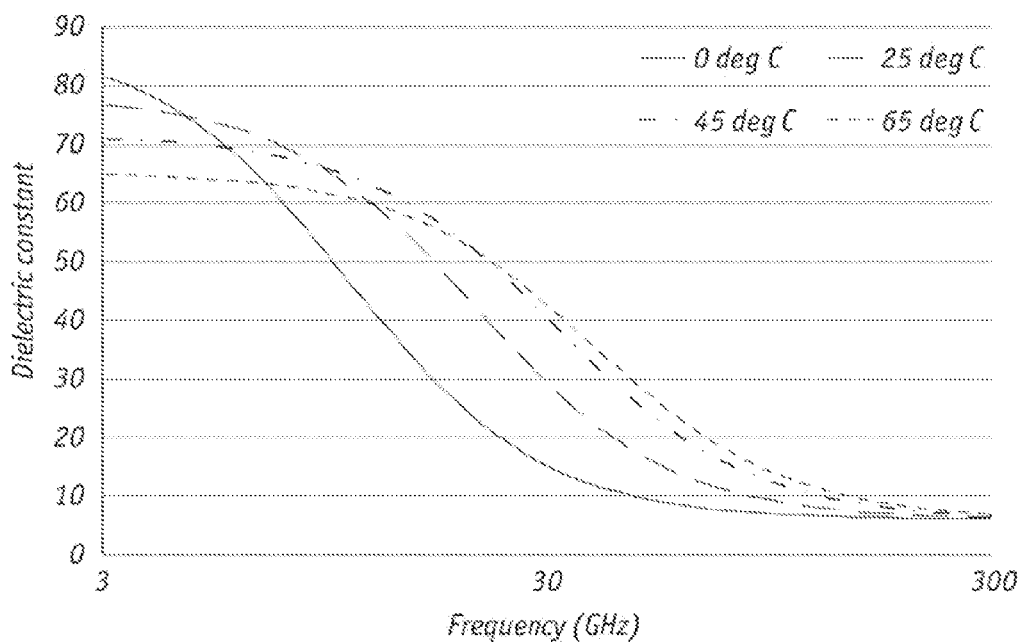
FIG. 3 is a graph of dielectric constant (the real part of permittivity) for free water as a function of frequency at 4 temperatures: just above freezing, 25° C., 45° C., and 65° C.
Figure 4:
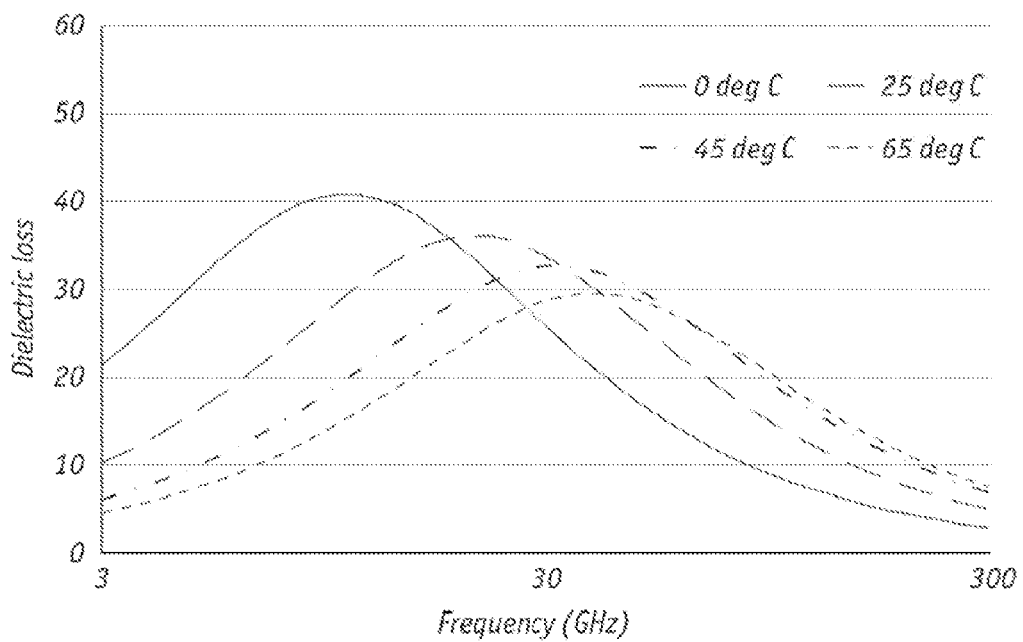
FIG. 4 is a graph of dielectric loss (the imaginary part of permittivity) for free water as a function of frequency at 4 temperatures: just above freezing, 25° C., 45° C., and 65° C.
Figure 5:
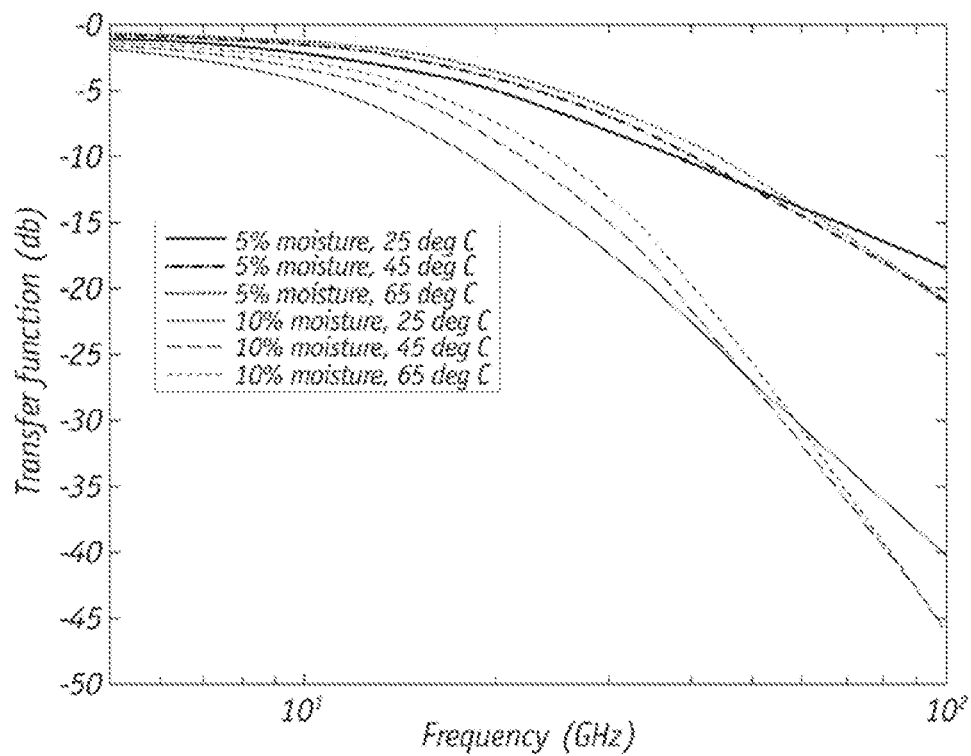
FIG. 5 is shows the transfer function of paper board as a function of moisture content and sheet temperature in the 5-100 GHz frequency range.

The main steps in the process for measuring one or more properties of a composition are shown in FIG. 2. In operation, the above-described microwave sensor in initial step 30 generates radiation in two or more frequency ranges and preferably in a wide frequency range. In practice, this is accomplished by generating microwaves over a spectrum of wavelengths which is directed into the sample material under test in step 32. The incident radiation interacts with the material and the radiation that emerges from the material is measured over the spectrum of wavelengths in terms of the amplitudes of the radiation in step 34. Step 36 is to calculate the sample transfer function. In this regard, FIGS. 3 and 4 are graphs of the dielectric constant and dielectric loss, respectively, for free water as a function of frequency at 4 temperatures: (i) just above freezing, (ii) 25° C., (iii) 45° C., and (iv) 65° C., according to the Debye model described above. FIG. 5 are the calculated transfer functions for paper board as a function of moisture content (5% and 10%) and sheet temperature (25° C., 45° C., and 65° C.) in the 5-100 GHz frequency range. The transfer function is the ratio of the measured amplitude with and without sample and the calculations are based on the model described above. Next, in step 38 the transfer function of the material is fitted into a model that has been developed. Finally, in step 40 the properties of interests, including for example, the moisture content, water temperature and basis weight of the material are extracted from the fit parameters using the previously established sensor calibration.

Figure 6:
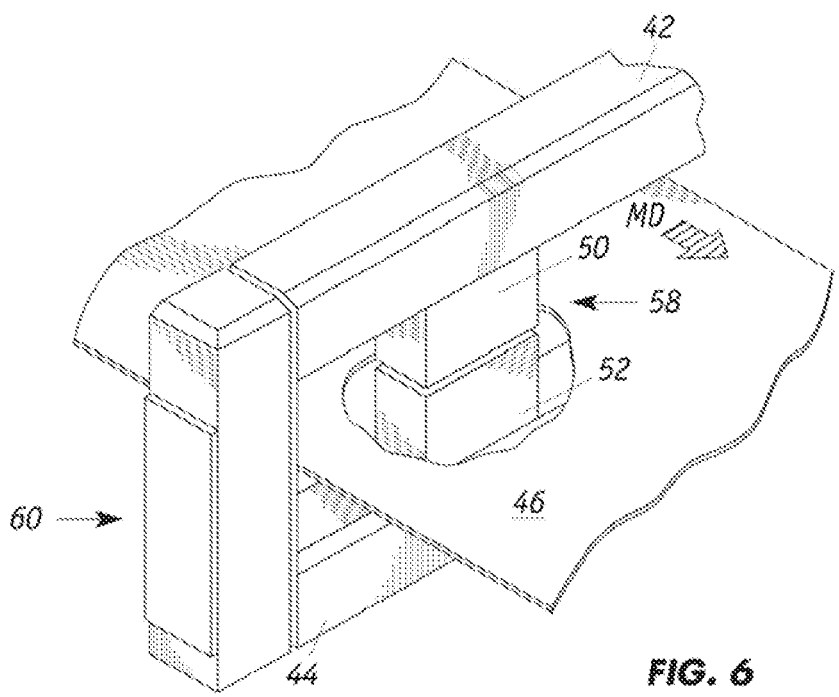
FIG. 6 illustrates scanning system incorporating a microwave sensor.

FIG. 6 illustrates one particular implementation of the microwave sensor whereby the sensor is incorporated into a dual head scanner 58 of scanner system 60 that is employed to measure properties of paper, board and like in a continuous production process. Upper scanner head 50, which houses the microwave source antenna, and lower scanner head 52, which houses the microwave receiver antenna, move repeatedly back and forth in the cross direction across the width of the moving sheet 46, which moves in the machine direction (MD), so that the characteristics of the entire sheet may be measured. Scanner 58 is supported by two transverse beams 42, 44, on which upper and lower scanning heads are mounted. The operative faces of the lower and upper scanner heads 52, 50 define a measurement gap that accommodates sheet 46. The movement of the dual scanner heads 52, 50 is synchronized with respect to speed and direction so that they are aligned with each other.

A technique of measuring wood material such as wood chips is to use a conveyer to continuously present the materials to a sensor of the presenting invention that is operating in the reflective mode. With a conveyer belt of limited width, sampling across the belt would not be necessary and a single stationary point measurement may suffice. Alternatively, stationary, multiple point measurements can be implemented.

The foregoing has described the principles, preferred embodiment and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A method of measuring two or more parameters of a composition, which includes water, that comprises the steps of:
   a. directing microwave radiation over a spectrum of wavelengths from an antenna to be incident upon the composition;
   b. measuring the microwave radiation over the spectrum of wavelengths that emerges from the composition;
   c. determining a reflected and/or transmitted transfer function of the composition over the spectrum of wavelengths;
   d. relating the determined transfer function of the composition over the spectrum of wavelengths to two or more parameters of the composition, that include water temperature and at least one of composition percent moisture or composition basis weight, by applying a model, with the proviso that an independent temperature measurement of the composition is not required; and
   e. predicting the water temperature and at least one of composition percent moisture or composition basis weight.

2. The method of claim 1 wherein step (d) comprises applying a multivariate model to the determined reflected and/or transmitted transfer function of the composition over the spectrum of wavelengths and predicting the two or more parameters.

3. The method of claim 2 wherein the model is a calibration model that is developed in a calibration process of collecting reference spectra over the spectrum of wavelengths from the calibration samples that contain the range of the two or more parameters values.

4. The method of claim 3 wherein the calibration process creates a calibration data set relating to a temperature dependence of the measured microwave radiation over the spectrum of wavelengths that emerges from the composition wherein the calibration data is generated in a temperature calibration step in which absorption of reference samples and having a range of temperatures is determined at various temperatures and at least two wavelengths and this calibration data is incorporated into the model.

5. The method of claim 1 wherein in step (d) the two or more parameters comprise water temperature, composition percent moisture, and composition basis weight and step (e) comprises predicting the water temperature, composition percent moisture and composition basis weight.

6. The method of claim 1 wherein step (b) measures the microwave radiation at two or more frequencies.

7. The method of claim 6 wherein the microwave radiation used in the measurement in step (b) has a frequency in the range of 1 MHz to 1 THz.

8. The method of claim 1 wherein the model incorporates a data set of effective transfer function of the composition that were calculated under different conditions.

9. The method of claim 1 wherein the model is a theoretical model.

10. The method of claim 1 wherein free parameters in the model are determined using calibration samples.

11. The method of claim 1 wherein the model is a hybrid of multivariable and equation based models.

12. The method of claim 1 wherein the microwave radiation is scanned along a cross direction of the composition.

13. A sensor for measuring at least two properties of a composition, which includes water, that comprises:
   an antenna, which emits microwave radiation over a spectrum of wavelengths at the composition;
   a receiver operable to detect reflected or transmitted radiation from the composition and to provide electrical detection signals;
   signal generator that generates first signals to the antenna to cause the antenna to emit microwave radiation at two or more frequencies at the composition and second signals that are indicative of the two or more frequencies; and
   a processor that receives the electrical detection signals and the second signal and that is operable to determine water temperature and at least one of composition percent moisture or composition basis weight by applying a model with the proviso that an independent temperature measurement of the composition is not required.

14. The sensor of claim 13 wherein the processor is operable to determine the water temperature, moisture percent moisture, and moisture basis weight.

15. The sensor of claim 13 wherein the receiver measures the microwave radiation at two or more frequencies.

16. The sensor of claim 15 wherein the microwave radiation used in the measurement in step (b) has a frequency in the range of 1 MHz to 1 THz.

17. The sensor of claim 13 wherein the source and receiver are on opposite sides of the composition and the signal is corrected to account for the distance between the source and the receiver as measured by a displacement sensor.

18. The sensor of claim 13 wherein the receiver is configured to operated in the reflective mode.

19. The sensor of claim 13 wherein the receiver is configured to operated in the transmissive mode.

20. The sensor of claim 13 wherein the antenna and receiver are scanned along a cross direction of the composition.

* * * * *